United States Patent
Sliwinski

(10) Patent No.: US 9,420,818 B2
(45) Date of Patent: Aug. 23, 2016

(54) THICKENER COMPOSITION FOR DYSPHAGIA PATIENTS

(75) Inventor: Edward Lucian Sliwinski, Oss (NL)

(73) Assignee: N.V. Nutricia, Zoetermeer (NL)

( * ) Notice: Subject to any disclaimer, the term of this patent is extended or adjusted under 35 U.S.C. 154(b) by 472 days.

(21) Appl. No.: 13/526,256

(22) Filed: Jun. 18, 2012

(65) Prior Publication Data

US 2012/0258195 A1 Oct. 11, 2012

Related U.S. Application Data

(63) Continuation of application No. 11/719,577, filed as application No. PCT/NL2004/000806 on Nov. 18, 2004, now abandoned.

(51) Int. Cl.
| | |
|---|---|
| A23L 1/30 | (2006.01) |
| A23L 1/0522 | (2006.01) |
| A23L 1/0526 | (2006.01) |
| A23L 1/0528 | (2006.01) |
| A23L 1/0534 | (2006.01) |
| A23L 1/054 | (2006.01) |
| A61K 31/715 | (2006.01) |

(52) U.S. Cl.
CPC ............ *A23L 1/30* (2013.01); *A23L 1/0522* (2013.01); *A23L 1/0526* (2013.01); *A23L 1/0528* (2013.01); *A23L 1/0534* (2013.01); *A23L 1/0541* (2013.01); *A61K 31/715* (2013.01); *A23V 2002/00* (2013.01)

(58) Field of Classification Search
CPC ........................................... A23L 1/30
USPC .......................................... 426/648
See application file for complete search history.

(56) References Cited

U.S. PATENT DOCUMENTS

| | | | |
|---|---|---|---|
| 3,721,571 A | 3/1973 | Glicksman | |
| 4,105,461 A | 8/1978 | Racciato | |
| 4,542,035 A | 9/1985 | Huang et al. | |
| 4,956,185 A | 9/1990 | Cajigas | |
| 5,429,837 A | 7/1995 | Balabaud et al. | |
| 5,597,603 A | 1/1997 | Cha et al. | |
| 6,277,395 B1 | 8/2001 | Fukui et al. | |
| 6,458,395 B1 * | 10/2002 | Emoto | ............ 426/72 |
| 6,461,589 B2 * | 10/2002 | Robbins | ......... 424/9.41 |
| 6,858,245 B2 | 2/2005 | De Coninck | |

(Continued)

FOREIGN PATENT DOCUMENTS

| | | |
|---|---|---|
| EP | 0 611 525 B1 | 3/1997 |
| EP | 0 745 330 B1 | 10/1998 |

(Continued)

OTHER PUBLICATIONS

"Simply Thick—the thickening gel you can't taste". Available online as of Jun. 2002 from www.simplythick.com. p. 1.*

(Continued)

*Primary Examiner* — Jenna A Watts
(74) *Attorney, Agent, or Firm* — Foley & Lardner LLP; Sunit Talapatra

(57) ABSTRACT

The invention relates to thickening compositions for thickening nutritional products to make the nutritional product suitable for consumption by dysphagia patients, said thickening composition comprising starch, xanthum gum and/or methylcellulose and galactomannan and/or glucomannan.

8 Claims, 2 Drawing Sheets

(56) References Cited

U.S. PATENT DOCUMENTS

| | | |
|---|---|---|
| 6,887,850 B2 | 5/2005 | Fuchs et al. |
| 2002/0014180 A1 | 2/2002 | De Coninck |
| 2003/0072729 A1 | 4/2003 | Szymczak et al. |
| 2003/0202992 A1 | 10/2003 | Fuchs et al. |
| 2007/0104700 A1 | 5/2007 | Garcia-Rodenas et al. |
| 2009/0074940 A1 | 3/2009 | Sliwinski |

FOREIGN PATENT DOCUMENTS

| | | |
|---|---|---|
| EP | 1 166 645 A2 | 1/2002 |
| EP | 1 431 313 A1 | 6/2004 |
| EP | 1 433 383 A1 | 6/2004 |
| EP | 1 313 376 B1 | 12/2005 |
| EP | 1 930 407 A1 | 6/2008 |
| EP | 1 930 407 B1 | 11/2009 |
| FR | 2699370 A1 | 6/1994 |
| FR | 2913857 A1 | 9/2008 |
| JP | 07-184569 A | 7/1995 |
| JP | 2000-191553 | 7/2000 |
| JP | 2003-245039 | 9/2003 |
| KR | 200290193 A | 11/2002 |
| KR | 3908470 | 9/2003 |
| WO | WO-01/01789 A1 | 1/2001 |
| WO | WO-03/011051 A1 | 2/2003 |
| WO | WO-03/055334 A1 | 7/2003 |
| WO | WO-2004-006179 A1 | 1/2004 |
| WO | WO-2006/054886 A1 | 5/2006 |
| WO | WO-2009/012889 A1 | 1/2009 |
| WO | WO 2010/120172 A1 | 10/2010 |

OTHER PUBLICATIONS

"Starch", Virtual Chembook, Elmhurst College. Available Mar. 23, 2015 from www.elmhurst.edu. p. 1.*

"Identification and Management of Dysphagia in Children with Neurological Impairment". "Best Practice", vol. 4, Issue 3, 2000. pp. 1-3.*

All Ayurveda.com website (accessed at www.allayayurveda.com/topic_month_april2009.asp) Apr. 2009.

Anderson Erickson Products—Cultured Lowfat Buttermilk (accessed at www.aedairy.com/products/cultured-lowfat-buttermilk/, publication date Jan. 3, 2009).

Blareau, et al. English machine translation of WO 1996/006924 (1996).

Huang, et al. "Feed thickener for newborn infants with gastro-oesophaeal reflux (Review)", The Cochrane Collaboration (2002) Issue 3, Article No. CD003211.

Vandenplas, et al. "A clinical trial with an "anti-regurgitation" formula", European Journal of Pediatrics (1994) vol. 153, pp. 419-423.

Sweet whey powder composition from Dairy for Global Nutrition website: http://www.dairyglobalnutrition.org. (2009).

"Formulating with tara gum: unique hydrocolloid provides economic and functional benefits". Available online Nov. 1997, Findarticles.com. pp. 1-2.

"Nutrition Facts and Calories (kcal) per 100 g wheat starch," http://translate.googleusercontent.com/translate_c?hl=en&sl=de&u=http://gesuender-abnehmen.com/abneh . . . , Feb. 7, 2011, 4 pgs.

Chau et al., "Chemical composition of three underutilized legume seeds grown in China," Science Direct, available on line Jun. 23, 1998, 1 page.

Definition of terms "powder" and "milling" taken from The American Heritage Dictionary of the English Language, retrieved from "The Free Dictionary" online on Aug. 25, 2009.

Galactomannan from Wikipedia, retrieved from http://en.wikipedia.org/wiki/Galactomannan, Jun. 11, 2009.

Glucomannan from Wikipedia, retrieved from http://en.wikipedia.org/wiki/Glucomannan, last modified Oct. 15, 2010, 3 pages.

International Search Report for PCT/NL2010/050192, dated Jul. 6, 2010, 3 pages.

International Search Report, PCT/NL2004/000806, dated Aug. 10, 2005, 3 pages.

Material Safety Data Sheet Xanthan gum MSDS, Science Lab.com, Oct. 11, 2005, pp. 1-6.

Miyazawa et al., "Effect of Locust Bean Gum in Anti-regurgitant Milk on the Regurgitation in Uncomplicated Gastroesophageal Reflux," Journal of Pediatric Gastroenterology and Nutrition, vol. 38, No. 5, May 2004, pp. 479-483.

Nutrition Facts and Calories (kcal) A & P sugar per 100 g, gesunder abnehmen, 2 pages (English astract found at http://translate.googleusercontent.com/translate_c?hl=en&sl=de&u=http://gesuender-abnehmen.com/abneh . . . , 4 pages).

Nutrition Facts and Calories (kcal) guar gum (guar gum) per 100 g, gesunder abnehmen, 2 pages (English abstract found at http://translate.googleusercontent.com/translate_c?hl=en&sl=de&u=http://gesuender-abnehmen.com/abneh . . . , 4 pages).

Nutrition Facts and Calories (kcal) 100 g of glucose, gesunder abnehmen, 2 pages (English abstract found at http://translate.googleusercontent.com/translate_c?hl=en&sl=de&u=http://gesuender-abnehmer.com/abneh . . . , 4 pages).

Nutrition Facts and Calories (kcal) UHT milk 3.5% per 100 g, gesunder abnehmen, 2 pages (English abstract found at http://translate.googleusercontent.com/translate_c?hl=en&sl=de&u=http://gesuender-abnehmen.com/abneh . . . , 4 pages).

Nutritional Information for: Gums, microbial (xanthan gum), FitDay, www.fitday.com/webfit/FoodFacts_outside.html?FoodID=42242&OwnerID=Fit Day, 2000, 2 pages.

Rote Bohnenpaste, from Wikipedia, http://de, wikipedia.org/wiki/Rote_Bohnenpaste, Sep. 28, 2009, 1 page (translation Red Bean Paste at http://translate.googleusercontent.com/translate_c?hl=en&sl=de&u=http:/// , , , 2 pages and at http://en.wikipedia.org/wiki/Red_Bean-paste, 5 pages).

Tomlin et al., "The effect of feeding xanthan gum on colonic function in man: correlation with in vitro determinants of bacterial breakdown," PubMed, PMID: 8329363, 1993, 1 page.

Xanthan Gum product material, C.E. Roeper GmbH, http://www.roeper.de/en/produktdetail.html?nummer=1851, last viewed Feb. 5, 2011, 2 pages.

* cited by examiner

THICKENER COMPOSITION FOR DYSPHAGIA PATIENTS

CROSS-REFERENCE TO RELATED APPLICATION(S)

This application is a continuation of U.S. application Ser. No. 11/719,577, filed Feb. 27, 2008, which is the National Phase of International Patent Application No. PCT/NL2004/000806, filed Nov. 18, 2004, published as WO 2006/054886. The contents of these applications are herein incorporated by reference in their entirety.

FIELD OF THE INVENTION

The invention relates to nutrition for dysphagia patients. Suitably the nutrition is in the form of thickened food. In particular the invention relates to a powdered nutritional product that can thicken a wide range of liquids or other foods. The invention further relates to a method for preparing food with a stable viscosity suitable for dysphagia patients.

BACKGROUND OF THE INVENTION

For healthy patients a better mouthfeel of a foodstuff can be a reason to eat it more often simply because they prefer the "taste" of it. For dysphagia patients things are however completely different. In fact a good mouthfeel may be considered a matter of life and death. Dysphagia patients are afraid to consume foodstuffs that appear to thin to them, because they fear to choke. This fear often shows by a reluctance to eat or drink and may lead to dehydration and mal-nutrition.

People with dysphagia generally lack proper muscle control and coordination to properly seal the windpipe or they lack the ability to properly propel the entire bolus of food and/or beverage to the stomach. For these reasons it is extremely important that the foodstuffs dysphagia patients consume have the proper viscosity when they judge the food visually and when they feel it in their mouth during consumption.

Thickening the beverages for humans afflicted with dysphagia is a common method of managing dysphagia. Thickening provides better bolus control, greater oral stimulation, and when swallowed, if incompletely propelled into the esophagus, it helps prevent undesired and potentially fatal aspiration of fluids into the lungs. Generally and most commonly, starch is used to thicken beverages of dysphagia patients. Starch is also the preferred ingredient in view of its properties, cost price, taste and thus acceptance by dysphagia patients.

For dysphagia patients several products are available for thickening liquids and foods. Such a thickening product is known from WO 2004/069179 where non-starch polysaccharides are used in thickened beverage compositions for the treatment of dysphagia patients. WO 01/01789 relates to a gelled nutritional composition including gelled whey protein suitable for dysphagia patients. WO 03/055334 describes a method for preparing thickened foods suitable for dysphagia patients wherein said binding, gelling or thickening compound is selected from the group consisting of proteins, carrageenans, starches, gums, gelatins, or a combination thereof. WO 03/011051 describes a concentrate thickener paste and the use thereof for thickening liquid food suitable for patients with dysphagia. The concentrate thickener is selected from at least one of alginates, carrageenan, galactomannans, cellulosics, food starches, xanthan gum and gum Arabic.

The disadvantage of the products presented in the prior art is that they do not combine all the necessary properties needed for treatment of dysphagia patients. WO 2004/069179 and WO 01/01789 describe the use of pre-thickened beverages or foods. These types of products are suitable for treating dysphagia patients but have the disadvantage of being unable to thicken other liquids or foods as is often not only required but also preferred by patients. In the method of WO 03/055334 and in document WO 03/011051 this problem is solved by using a thickener suitable for thickening any food. However WO 03/055334 and WO 03/011051 only describe a method for preparing thickened food but do not solve the important problem that the product is not stable during consumption due to the activity of amylase from saliva. The invention of WO 03/055334 is not related to the problem of preparing a thickener composition. WO 03/011051 relates to a concentrate thickener paste for thickening liquids and indicates in the text that the use of powders as thickening agents is disadvantageous due to clumping caused by bad hydration properties. Due to the water retaining properties of xanthan gum in the colon, the preferred embodiment of WO 03/055334 where xanthan gum is used as a thickening agent, has the disadvantage of retaining water in the gut. It is known that dysphagia patients often suffer from dehydration. The use of xanthan gum is therefore a disadvantage and the xanthan gum content in the thickened products should preferably be as low as possible.

SUMMARY OF THE INVENTION

In the preparation of food for dysphagia patients several aspects and properties are of crucial importance in order to arrive at successful consumption by and proper nutrition of dysphagia patients.

First of all the mouthfeel and corresponding viscosity is very important. Before consumption the product should give the dysphagia patient the impression that it is thickened properly and has the right viscosity.

Secondly, dysphagia patients often spill saliva during consumption and need a relatively long time to consume their food. When starch is used as a thickener the amylase present in the saliva will digest the starch and the viscosity of the product will decrease. This leads to an undesirable decrease in viscosity that again increases the problems for dysphagia patients to swallow the food. It is therefore essential that the food dysphagia patients consume retains the right viscosity during consumption.

Further, the preparation of the food product for dysphagia patients in elderly homes, hospitals, nursing homes etc., includes freezing of the prepared thickened foods and thawing the food before consumption. It is very important that the viscosity of the thickened product before freezing and after thawing stays constant. In that way the patient will always receive a product with a constant viscosity so that (s)he will feel confident when consuming the product. It is therefore essential that the food dysphagia patients consume retains the right viscosity during preparation.

Therefore the object of the present invention is to provide a product that combines the properties of a good viscosity profile (mouth feel) and a good stability during consumption (i.e. resistance against amylase digestion) as well as a good stability during preparation (i.e. freeze-thawing).

The present inventors found that when xanthan gum in combination with galactomannan such as tara gum, is mixed with starch, a food thickening agent is obtained which complies with all essential properties of a thickening agent suitable for dysphagia patients. A small quantity of gums in combination with starch gives an ideal viscosity profile while the gums protect the starch from degradation by amylase during the consumption of the thickened foods.

Thus the invention concerns a method for thickening nutritional products to make the nutritional product suitable for dysphagia patients by mixing starch, at least one selected from xanthan gum and methylcellulose, and at least one selected from galactomannan and glucomannan with the nutritional product.

More in particular, the invention concerns the use of a composition comprising starch, at least one selected from the group consisting of xanthan gum and methylcellulose, and at least one selected from the group consisting of galactomannan and glucomannan for the preparation of a nutritional product that is suitable for dysphagia patients.

DESCRIPTION OF THE INVENTION

The term "comprising" is to be interpreted as specifying the presence of the stated parts, steps or components, but does not exclude the presence of one or more additional parts, steps or components.

Starch can be described as alfa-1,4 linked polyglucose. In the context of this invention starch is food grade starch that can be commercially obtained from numerous suppliers. Besides starch from potatoes, suitable starches may be corn-, rice-, wheat- and tapoica starch. For example a suitable starch is waxy maize starch (e.g WMS 78-0632 from National Starch).

Xanthan gum is a high molecular weight, long chain polysaccharide composed of the sugars glucose, mannose, and glucuronic acid. The backbone is similar to cellulose, with added side chains of trisaccharides. In the context of this invention xanthan gum is food grade and can be commercially obtained from numerous suppliers. Suitable xanthan is for instance Novaxan (dispersible, transparant) from ADM and for instance Rhodigel Supra Clear supplied by Rhodia. In the context of this invention methylcellulose is food grade and can be commercially obtained from numerous suppliers.

Galactomannan is a gum in which the structural chain is made up of D-mannose units with beta-1,4 linkages, having (single) side chains of galactose units. The ratio of galactose to mannose differs in different galactomannans, with usually the majority being mannose. Glucomannan is a polysaccharide comprised of D-glucose and D-mannose residues bonded together in beta-1,4 linkages. Ususally approximately 60% of the polysaccharide is made up of D-mannose and approximately 40%, of D-glucose. In the context of this invention galactomannan and glucomannan are food grade and can be commercially obtained from numerous suppliers In one embodiment the dry components starch, xanthan and/or methylcellulose and galactomannan and/or glucomannan are mixed to give a dry thickener composition, suitably a dry powder. Dissolution of this dry composition in food products can be aided by including maltodextrin in the dry composition, which prevents the formation of lumps in the food product. Thus the use of the composition of the invention including maltodextrin is a further embodiment of this invention. It is preferred the composition is used in the form of a dry powder. Maltodextrin can be described as polymers of dextrose. In the context of this invention maltodextrin is food grade and can be commercially obtained from numerous suppliers As already mentioned it is important that the starch containing nutritional product retains suitable viscosity while being consumed by dysphagia patients. A measure for the viscosity which reflects the degradation by amylase is the measure wherein the force to compress a nutritional product is reduced after treatment with saliva compared to the untreated nutritional product. The conditions for treatment with saliva and measurement of compression are described in example 2. A nutritional product is considered suitable for dysphagia patients if after the treatment with saliva the compression of the nutritional product is not reduced by more than 20%. Thus in one embodiment the invention concerns a thickening composition for thickening nutritional products to make the nutritional product suitable for consumption by dysphagia patients, said thickening composition comprising starch, at least one selected from xanthan gum and methylcellulose, at least one selected from galactomannan and glucomannan and optionally maltodextrin, wherein compression of the nutritional product is not reduced by more than 20% after treatment of the nutritional product with saliva compared to the untreated nutritional product as measured using a TA.XT.Plus Texture Analyser.

Further the invention concerns a thickening composition for thickening nutritional products to make the nutritional product suitable for consumption by dysphagia patients. In an embodiment the thickening composition comprises, based on the total dry weight of the product, 20-90 wt. % starch, 0.1-10 wt. % of at least one selected from xanthan gum and methylcellulose and 0.4-30 wt. % of at least one selected from galactomannan and glucomannan and in addition the composition comprises up to 55 wt. % maltodextrin. In one embodiment starch, xanthan gum and/or methylcellulose, galactomannan and/or glucomannan and maltodextrin are in total more than 80 wt. %, suitably essentially 100 wt. %, of the dry weight of the thickening composition. Preferably the thickening composition is in the form of a dry powder. Suitably the thickening composition is used to thicken liquids and/or liquefied foods such as beverages and dairy products, vegetables such as carrots, spinach, etc and meat that are liquefied by blending, mincing and/or grinding.

In one embodiment in the use and compositions of the present invention xanthan gum is selected. In another embodiment galactomannan is selected, and in yet a further embodiment xanthan gum and galactomannan are selected.

In the present invention suitably galactomannan is selected from the group consisting of guar gum, locust bean gum, tara gum, fenugreek gum, cassia gum and a suitable glucomannan is konjac mannan, preferably tara gum is selected.

A preferred embodiment of the thickening composition according to the invention is as follows:
based on dry weight of the composition:

|  |  | more preferably |
|---|---|---|
| starch | 20-90 wt. % | 40-70 wt. % |
| tara gum | 0.4-30 wt. % | 4-20 wt. % |
| xanthan gum | 0.1-10 wt. % | 1-5 wt. % |
| maltodextrin | 0-55 wt. % | 15-55 wt. % |

As is depicted in table 1, the inventors surprisingly found that only a combination of starch with galactomannans (e.g. tara gum) and xanthan results in a food product that is stable during both freeze-thawing and amylase treatment.

Table 1 shows the results of a stability test wherein thickened water was tested without further treatment, treated with amylase and treated by freezing and thawing of the thickened product. The results show that only when starch is combined with tara gum and xanthan gum the product retains its viscosity after both treatments.

TABLE 1

Amylase resistance and freeze-thaw stability (Compression force measured in triplicate in grams)

|  | starch | starch + tara gum | starch + xanthan gum | starch + tara gum + xanthan gum (see example 2) |
|---|---|---|---|---|
| Without treatment | 31 | 37 | 29 | 49 |
| With amylase | 19 | 29 | 28 | 48 |
| Freeze and thaw | 30 | 42 | 22 | 49 |

The starch + xanthan gum + tara gum combination is the most stable during both the amylase treatment and the freeze/thaw treatment.

Further the present invention concerns a thickened nutritional product comprising protein, fat and a thickener composition according to the present invention, said thickened nutritional product having an energy density between 1.3-2 kcal/ml.

Also the invention relates to a method for preparing a thickened nutritional product comprising the steps of mixing the thickener composition according to the present invention with a food product and optionally followed by the steps of freezing the thickened nutritional product thus obtained and thawing the frozen nutritional product.

Fermentation Characteristics and Water Retention of the Thickeners

Fibers such as xanthan gums are known to retain water in the colon. When colon bacteria ferment fibers, the water bound to the fibers will be released and available for absorption over the gut barrier. The inventors surprisingly found that tara gum is much better fermented by intestinal flora bacteria than xanthan gum (FIG. 2). This indicates that water retention by tara gum is less than by xanthan gum. Therefore the composition should preferably contain more tara gum than xanthan gum. Another advantage of this surprising finding is that because tara gum is better fermentable, it will produce more short chain fatty acids that are beneficial for gut health. Based on the results of the fermentation characteristics of xanthan and tara gum it is preferred to have a composition comprising more tara gum than xanthan gum. Suitably the weight ratio of starch:xanthan gum and/or methylcellulose and galactomannan and/or glucomannan is in the range of 1:4 to 1:10, also the weight ratio of xanthan gum and/or methylcellulose:galactomannan and/or glucomannan is in the range of 1:4 to 1:10.

EXAMPLES

Example 1

Viscosity Profile

Figure 1:
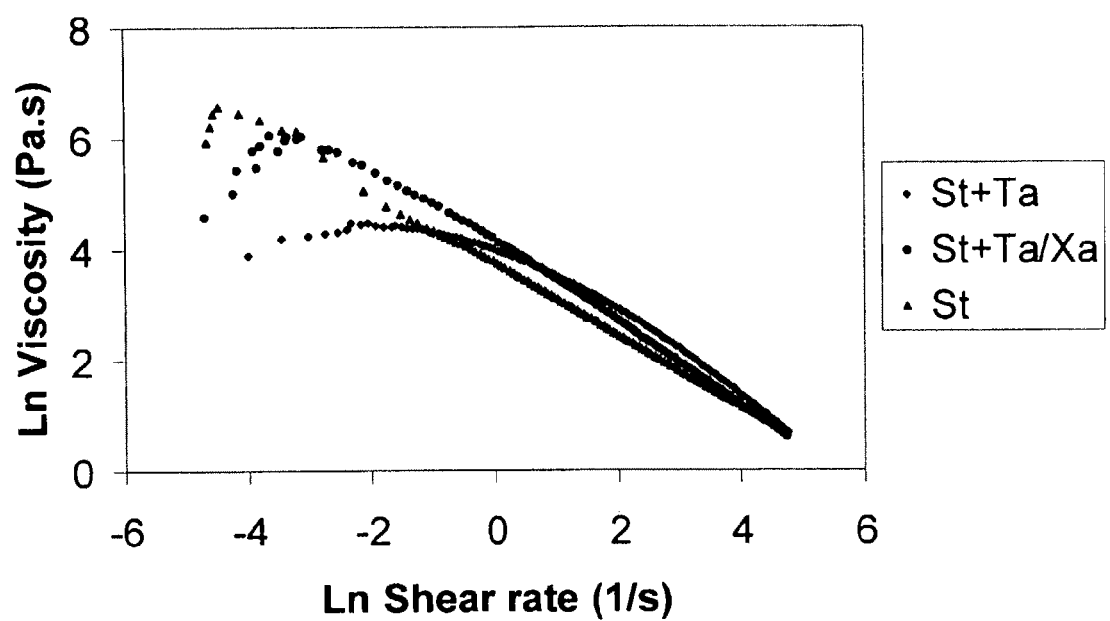
FIG. 1 shows the ideal viscosity profile (St), the profile of a composition consisting of starch and tara gum (St+Ta) and starch with tara gum and xanthan gum (St+Ta/Xa). From the figure it can be seen that the composition with both tara gum and xanthan gum gives a viscosity profile close to the ideal profile.
Figure 2:
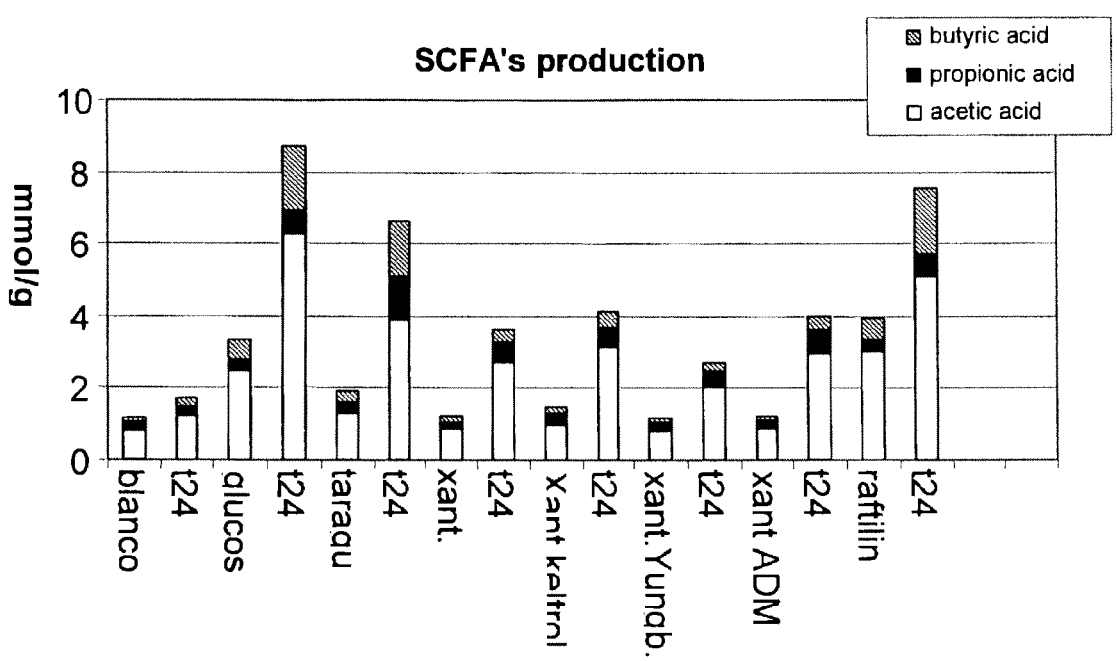
FIG. 2 shows the fermentation of gums and starch by intestinal flora bacteria. As can be seen from this figure, xanthan gum is not well hydrolyzed while tara gum is comparable with glucose. This indicates that xanthan will only be fermented for a small part and therefore has the effect of retaining water in the faeces. In dysphagia patients, this water retention is undesirable because many patients already have dehydration problems due to low intake of liquids.

During processing in the mouth and swallowing the viscosity of a food product changes due to shear forces. This change in viscosity can be analyzed in a laboratory mixing experiment of the food product. The force needed for mixing food product is a measure for the viscosity of this food product. As can be seen in FIG. 1, the viscosity decreases when the shear rate increases.

Consumers are accustomed to the ideal viscosity profile of a product entirely consisting of starch. This product is depicted as triangles (St) in FIG. 1. It was found that by combining tara gum, xanthan gum and starch a similar viscosity profile could be made depending on the quantity and ratios of these ingredients. Tara gum or xanthan gum alone were not able to mimic the viscosity profile. Tara gum and xanthan gum could be replaced or mixed with other polysaccharide gums of plant and microbial origin as there are locust bean gum, guar gum, fenugreek gum, tamarind gum, konjac mannan, cassia gum, gum Arabic, gum ghatti, pectin, cellulosics, agar, carrageenan, alginate, tragacanth gum, karaya gum, curdlan and gellan gum.

Preparation of Dispersions

Dispersions were prepared by adding 12 gram of thickener composition described in Example 4 to 200 gram of water in a 500 ml shaking beaker and shaking the mixture in the shaking beaker by hand until no powder particles could be observed anymore visually. After preparation the dispersions were allowed to rest for 15 minutes at 20° C.

Measurement of Viscosity in Shear

The viscosity was determined using a Carri-Med CSL rheometer. The used geometry is of conical shape (6 cm 2 deg acrylic cone) and the gap between plate and geometry was set on 55 µm. A logarithmic continuous ramp shear rate was used from 1 to 1000 $s^{-1}$ in 2 minutes. The rheometer's thermostat was set on 20° C.

Example 2

Compression Test

Preparation of Dispersions

Dispersions were prepared by adding 12 gram of a thickener composition described in Example 4 to 200 gram of water in a 500 ml shaking beaker and shaking the mixture in the shaking beaker by hand until no powder particles could be observed anymore visually. Directly after preparation of the dispersion it was split in two and transferred to 100 ml cups. After preparation the dispersions were allowed to rest for 30 minutes at room temperature.

Freeze-Thaw-Heat Treatment

After preparation the dispersions were put in a freezer with a temperature of −18° C. and were left in the freezer overnight. Before a measurement dispersions were taken out of the freezer and heated up to 90° C. in a Micro-Wave. After heating the dispersions were allowed to rest and cool down for 30 minutes.

Treatment with Saliva

Fresh human saliva from one or more individual(s) was gathered and mixed carefully. Directly after fresh preparation of a dispersion, or 30 minutes after a dispersion had been heated 2 ml of the saliva-mixture was carefully applied on top of the dispersions using a pipette. Care was taken that the upper surface of the dispersion was not disturbed when applying saliva. After addition of the saliva the dispersions were incubated at 20° C. for one hour.

Measurement of Compression Force

To make sure the dispersions would be compressed exactly in the centre they were placed in a specially developed mall precisely under the compression disc. The dispersions were compressed using a TA.XT.Plus Texture Analyser (Stable Micro Systems, Godalming, UK) equipped with an acrylic 35 mm circular disc at 20° C. Before testing the disc was lowered at a pre-test speed of 1.5 mm/sec until a trigger force was measured of 5 g. During testing the disc was lowered at a test speed of 2 mm/sec until a depth of 20 mm. After compression the disc was moved upwards at a constant speed of 2 mm/sec. During the test the force required to compress and de-compress the dispersion and the distance the disc traveled were recorded. For further calculations the maximum compression force was used. Tests were performed 3 times and average is depicted in table 1.

Example 3

Fermentation of Gums

Microorganisms

Micro-organisms were obtained from fresh faeces from bottle fed babies. Fresh faecal material from babies ranging 1 to 4 month of age was pooled and put into preservative medium within 2 h.

Compositions/Substrate

As substrate either prebiotics (TOS; TOS and inulin HP mixture in a 9/1 (w/w) ratio; inulin HP; oligofructose and inulin HP mixture in a 1/1 (w/w) ratio, or none (blanc) was used.

Media

McBain & MacFarlane medium: Buffered peptone water 3.0 g/l, yeast extract 2.5 g/l, mucin (brush borders) 0.8 g/l, tryptone 3.0 g/l, L-Cysteine-HCl 0.4 g/l, bile salts 0.05 g/l, K2HPO4.3H2O 2.6 g/l, NaHCO3 0.2 g/l, NaCl 4.5 g/l, MgSO4.7H2O 0.5 g/l, CaCl2 0.228 g/l, FeSO4.7H2O 0.005 g/l. Fill 500 ml Scott bottles with the medium and sterilize 15 minutes at 121° C.

Buffered medium: K2HPO4.3H2) 2.6 g/l, NaHCO3 0.2 g/l, NaCl 4.5 g/l, MgSO4.7H2O, 0.5 g/l, CaCl2 0.228 g/l, FeSO4.7H2O 0.005 g/l. Adjust to pH 6.3±0.1 with K2HPO4 or NaHCO3. Fill 500 ml Scott bottles with the medium and sterilize 15 minutes at 121° C.

Preservative medium: Buffered peptone 20.0 g/l, L-Cysteine-HCl 0.5 g/l, Sodium thioglycollate 0.5 g/l, resazurine tablet 1 per liter, adjust to pH 6.7±0.1 with 1 M NaOH or HCl. Boil in microwave. Fill 30 ml serum bottles with 25 ml medium. Sterilize 15 minutes at 121° C.

The fresh faeces are mixed with the preservative medium and can be preserved in this form for several hours at 4° C.

Faecal suspension: The preserved solution of faeces is centrifuged at 13,000 rpm for 15 minutes. The supernatant is removed and the faeces is mixed with the McBain & Mac Farlane medium in a weight ratio of 1:5.

Fermentation 3.0 ml of the faecal suspension were combined with 85 mg glucose or prebiotic or with no addition (blanc) in a bottle and mix thoroughly. A t=0 sample was withdrawn (0.5 ml). 2.5 ml of the resulting suspension is brought in a dialysis tube in a 60 ml bottle filled with 60 ml of the buffered medium. The bottle was closed well and incubated at 37° C. Samples were taken from the dialysis tube (0.2 ml) or from the dialysis buffer (1.0 ml) with a hypodermic syringe after 3, 24, and 48 hours and immediately put it on ice to stop fermentation.

Short Chain Fatty Acids Analysis

The short chain fatty acids (SCFA) acetic, propionic, n-butyric, iso-butyric and n-valeric acids were quantitatively determined by a Varian 3800 gas chromatograph (GC) (Varian Inc., Walnut Creek, U.S.A.) equipped with a flame ionisation detector. 0.5 µl of the sample was injected at 80° C. in the column (Stabilwax, 15×0.53 mm, film thickness 1.00 µm, Restek Co., U.S.A.) using helium as a carrier gas (3.0 psi). After injection of the sample, the oven was heated to 160° C. at a speed of 16° C./min, followed by heating to 220° C. at a speed of 20° C./min and finally maintained at a temperature of 220° C. for 1.5 minutes. The temperature of the injector and detector was 200° C. 2-ethylbytyric acid was used as an internal standard.

Example 4

50.0% modified waxy maize starch (WMS 78-0632 from National Starch),
39.6% maltodextrin (27.9% Glucidex 19 IT from Roquette and 11.7% C*Dry from CereStar),
9.0% tara gum (tara gum High Viscosity from Exandal Corp.),
1.4% xanthan gum (Novaxan (dispersible, transparant) from ADM).

Example 5

50% modified waxy maize starch (US-M from National Starch),
8% konjac gum (VidoGum KJ II, Unipektin)
2% Xanthan gum (Rhodigel Supra Clear, Rhodia)
40% maltodextrin Example 6

50% modified starch
10% tars gum
2% methylcellulose (Akucell AF 2985, Akzo Nobel)
38% maltodextrin Example 7

Preparation of a Thickened Meal 1. products (e.g. vegetables) are cleaned and if necessary thawed
2. product is mixed in blender together with e.g. milk and/or water and/or butter
3. thickener composition is added and mixed with blended product
4. obtained thickened product is put in malls shaped in a attractive form
5. product is frozen
6. the frozen product is released from the mall and thawed
7. heated in oven until 72° C. to 83° C. as a pasteurisation step
8. cooling the product until desired temperature for consumption Product prepared in this way using e.g. the composition of one of the previous examples will give a stable product resistant to amylase digestion.

The invention claimed is:
1. A method of providing nutrition to a patient suffering from dysphagia, the method comprising administering to the patient in need thereof a nutritional food product comprising a composition, based on the total dry weight of the composition, comprising:
- (a) 40-70 wt. % starch;
- (b) 1-5 wt. % xanthan gum, methylcellulose, or both;
- (c) 4-20 wt. % tara gum; and
- (d) 15-55 wt. % maltodextrin, wherein the weight ratio of ingredients (b):(c) is in the range of 1:4 to 1:10.

2. The method according to claim 1, wherein ingredients (a)-(d) comprise more than 80 wt. % of the dry weight of the composition.

3. The method according to claim 1, wherein the composition is in the form of a powder.

4. The method according to claim 1, wherein the nutritional product has an energy density between 1.3-2 kcal/ml.

5. A method of providing nutrition to a patient suffering from dysphagia, the method comprising:
- (a) mixing a nutritional food product with a composition comprising, based on the total dry weight of the composition:
  - (i) 40-70 wt. % starch;
  - (ii) 1-5 wt. % xanthan gum, methylcellulose, or both;
  - (iii) 4-20 wt. % tara gum; and
  - (iv) 15-55 wt. % maltodextrin, wherein the weight ratio of ingredients (ii):(iii) is in the range of 1:4 to 1:10, and
- (b) administering the resulting nutritional product to the dysphagic patient in need thereof.

6. The method according to claim 5, wherein ingredients (a)-(d) comprise more than 80 wt. % of the dry weight of the composition.

7. The method according to claim 5, wherein the composition is in the form of a powder.

8. The method according to claim 5, wherein the resulting nutritional product has an energy density between 1.3-2 kcal/ml.

* * * * *